United States Patent [19]
Shepherd

[11] Patent Number: 5,259,103
[45] Date of Patent: Nov. 9, 1993

[54] SYSTEM FOR REMOVING RADIATION SOURCES FROM BRAIN IRRADIATING APPARATUS

[76] Inventor: J. L. Shepherd, 1010 Arroyo Ave., San Fernando, Calif. 91340

[21] Appl. No.: 853,131

[22] Filed: Mar. 18, 1992

[51] Int. Cl.⁵ ............................................. B23P 19/00
[52] U.S. Cl. .................. 29/426.3; 29/426.5; 29/723; 29/906
[58] Field of Search ............... 29/426.1, 426.2, 426.3, 29/426.4, 426.5, 426.6, 720, 723, 906, 402.03, 402.08; 250/308

*Primary Examiner*—Joseph M. Gorski
*Attorney, Agent, or Firm*—Wagner & Middlebrook

[57] ABSTRACT

In a brain irradiating system a large number of Cobalt 60 radiation sources are carried in ports in a heavy primary shield. After the normal ten year useful life of such radiation sources, they are often difficult to remove because due to corrosion, etc. the aluminum source holders become fused in their ports. The apparatus herein includes a hollow collet which grasps the head of the source holder surrounded by and, preferably, splined to a mechanical puller which securely holds the collet around the source holder cap. Liquid nitrogen is caused to flow into the hollow collet and against the cap of the source holder, causing the aluminum source holder to shrink more than the surrounding steel of the primary shield. The source holder and the Cobalt 60 source may then be either pulled out or, if threadedly engaged with the primary shield, turned out of its port. A second embodiment used where the above system fails to remove the source, involves members grasping the cap of the source holder, holding it centered, and using a hollow core drill, drilling the source holder out and away from its port while securely capturing the cobalt 60 source capsule within the hollow core drill bit. Following either of the above procedures, the source holder and the cobalt 60 capsule are deposited in a suitable shielded container.

11 Claims, 3 Drawing Sheets

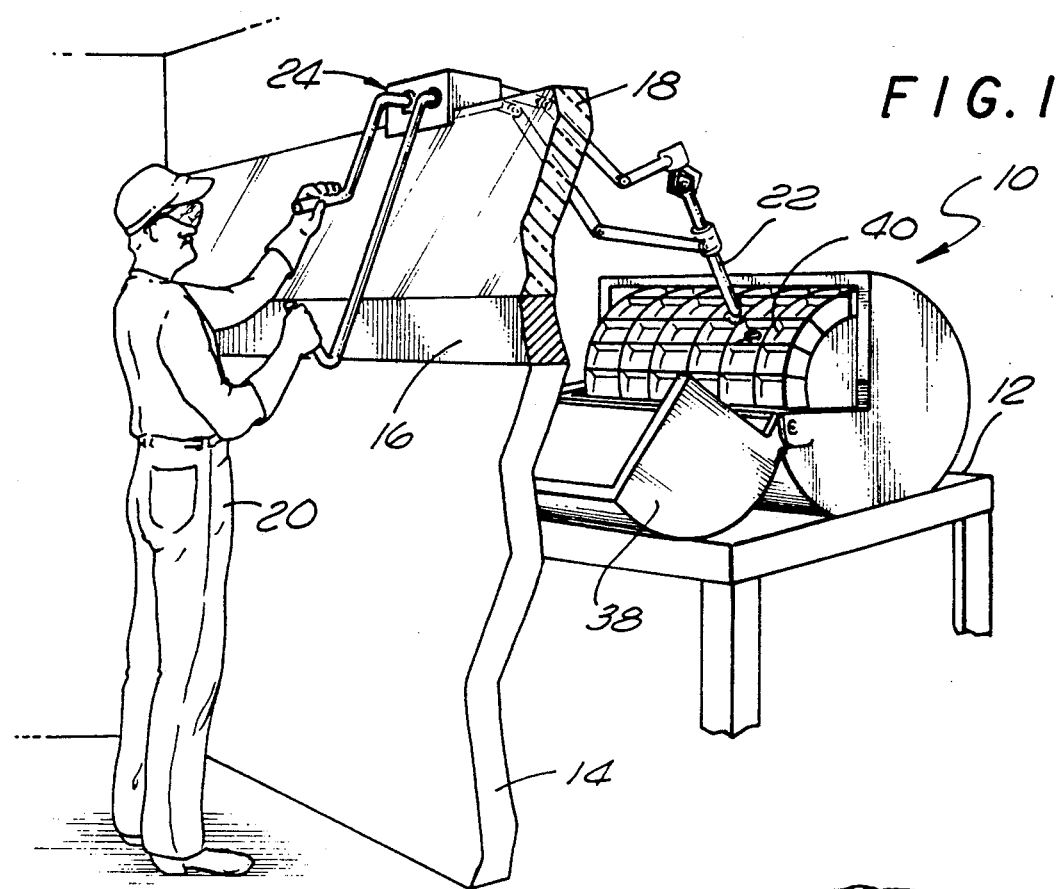
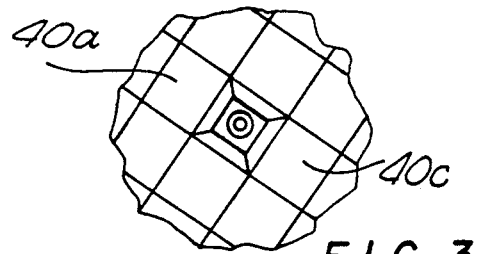
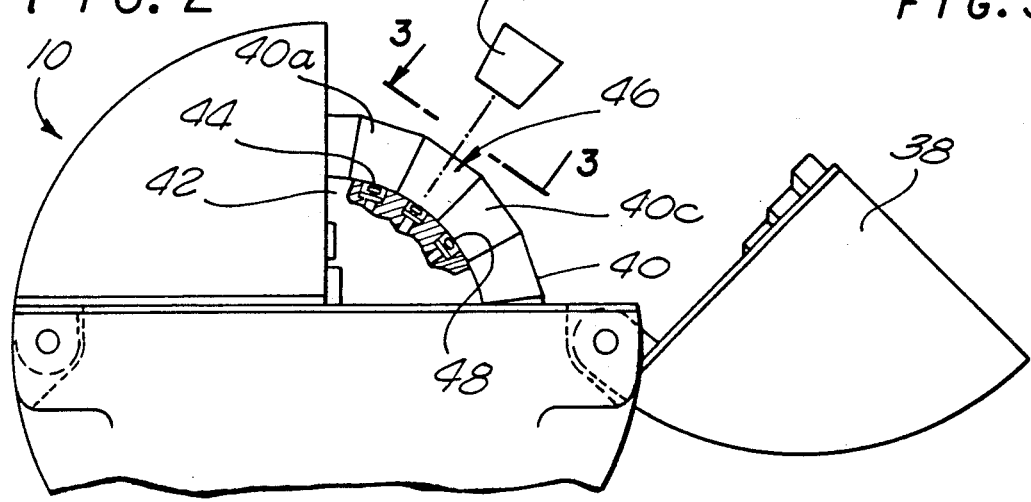

5,259,103

SYSTEM FOR REMOVING RADIATION SOURCES FROM BRAIN IRRADIATING APPARATUS

BACKGROUND OF THE INVENTION

In the many years of the use of radiation sources for irradiating objects or (in the medical field) patients, the design of radiation equipment has taken into account the safeguards for personnel in placing and using radiation sources. Usually this involves the presence of large bodies of lead surrounding the radiation source with provision for limited exposure of the radiation source to provide the required radiation followed by shielding at the end of the radiation period.

Often the shielding takes the form of a full shielded room. More often it involves a shielded room plus shielding in the equipment itself. Much of such equipment is configured such that it must be shipped without a radiation source in place and is then installed. The radiation source is then inserted within a shielded room or within temporary lead barriers with remotely controlled manipulatory means.

Many such pieces of radiation equipment have been installed throughout the world, used and the radiation sources have become exhausted from the operational standpoint but are still hazardous to unshielded personnel. An example of such an application involves systems for irradiating a patient's cranium with gamma particles from a Cobalt 60 source. Such equipment has been known and widely sold by Eleckta Corporation of Sweden and is known as Gamma Knife apparatus. Cobalt 60 has a half life of 5.2 years and a practical period for removal and replacement of the radiation source has been determined to be 10 years. In one such type of equipment, approximately 200 radiation sources are located within a hemispheric shield. Typically this requires the steps of:

1. setting up a portable shielded facility with a viewing window and remote handlers in the room in which the equipment is located;
2. raising the top cover of the apparatus;
3. removal of screw fasteners and restraining pins which secure aluminum source holders within a steel primary shield;
4. grasping and removing the aluminum source holder with tongs using the remote handlers or unthreading the aluminum source holder from the primary shield; and
5. transferring the source in the aluminum source holder with remote tongs to a shielded shipping container.

Steps 3-5 must be repeated for every source of which there may be 179 or 201 in currently available equipment.

Because of the tight tolerances employed in manufacturing the Cobalt 60 source, the aluminum holder in which the source is mounted and the steel or cast iron primary shield into which the source mounted in the aluminum holder is placed, which is typically 0.1 mm for the complete assembly, and because of the corrosion which occurs over a five to ten year period of use before source reloading, it has been found that sources often cannot be removed using the above standard techniques. Typically, a significant portion such as 50 percent are not removable using the standard technique. Thus there is a need for a method and apparatus capable of removing these sources.

BRIEF DESCRIPTION OF THE INVENTION

After the portable shielding has been erected in the room in which the irradiation equipment is located, an upper shield, which is hinged will be opened and a new upper shield which has removable sections is installed. This new temporary upper shield then provides full shielding for all the sources except 1 to 4 which are to be worked on. This permits subsequent source removal to take place using a small portable shielding wall erected next to the radiation unit and permits direct manipulation of the sources using simple over the wall handling equipment rather than the complex manipulators used previously. Viewing may be by remote television or simple mirror techniques.

For those units in which source holders are held in place by "U" shaped pins secured by screws, the screws are removed, either by unthreading or by grinding if the screws are corroded; and the pin is removed. A hollow collet precision shaped to fit over and grasp the cap of the aluminum source holder is lowered over the head of the source holder and engaged. The collet is precisely located over the head of the holder by a ring which fits into an indentation in the primary shield and which is lowered over the head of the aluminum source holder. Liquid nitrogen is then introduced through the hollow section of the collet for approximately five to fifteen minutes to differentially shrink the aluminum source holder to a smaller diameter. The aluminum source holder will shrink to a greater extent than the steel or cast iron primary shield into which it is fitted because of the greater coefficient of thermal expansion of aluminum as compared to the steel or cast iron holder. Hydraulic or mechanical pressure is then exerted on the collet to remove the aluminum source holder with its internal source. The source holder is then remotely transferred to a suitable shipping cask.

For those units in which the aluminum source holder is threaded into the steel or cast iron pressing shield, a hollow collet is supplied which fits over and grasps the head of the aluminum source holder using a ring to precisely locate the collet over the source holder. This collet is set up so that rotary motion can be mechanically applied. Liquid nitrogen is then introduced into the hollow section of the collet as described above. After five to fifteen minutes rotary force is applied to turn the source holder and unthread it from the primary shield. Force limits are used to avoid fracturing the aluminum source holder. The source holder is then remotely transferred to a shipping cask as described above.

In the event the aluminum source holders of either type cannot be removed by the techniques and with the equipment described above, applicant herein has devised an additional technique and apparatus to accomplish the desired removal. A hollow core drill with an outside diameter smaller than the opening in the steel or cast iron primary shield and with inside diameter larger than the outside diameter of the stainless steel Cobalt 60 source capsule is employed to selectively drill through the aluminum source holder without damaging either the Cobalt 60 source inside the holder or the primary shield. A locating ring for the core drill will be set up to precisely locate the drill over the aluminum source holder. The core drill is mounted on a short quill and chuck which is mechanically driven to cut through the aluminum source holder. The entire drill assembly is fixed to the exterior of the primary shield by means of an especially designed and constructed electromagnet. After the aluminum source holder has been drilled through, it will remain inside the core drill which is removed from the drill shaft by a quick disconnect device and the core drill carrying the aluminum source holder with the Cobalt-60 source inside is then transferred to an adjacent shipping shield.

BRIEF DESCRIPTION OF THE DRAWINGS

This invention may be more clearly understood from the following detailed description and by reference to the drawings in which:

FIG. 1 is a perspective drawing of a typical brain irradiator apparatus with my radiation source removal equipment in position to remove a radiation source holder;

FIG. 2 is an end view, partly in section, of a brain irradiation apparatus with a hinged upper shield shown partly open and with a temporary upper shield installed and a section thereof shown displaced to expose a radiation source holder;

FIG. 3 is a fragmentary plan view of the temporary upper shield taken along line 3—3 of FIG. 2;

DETAILED DESCRIPTION OF THE INVENTION

Figure 4:
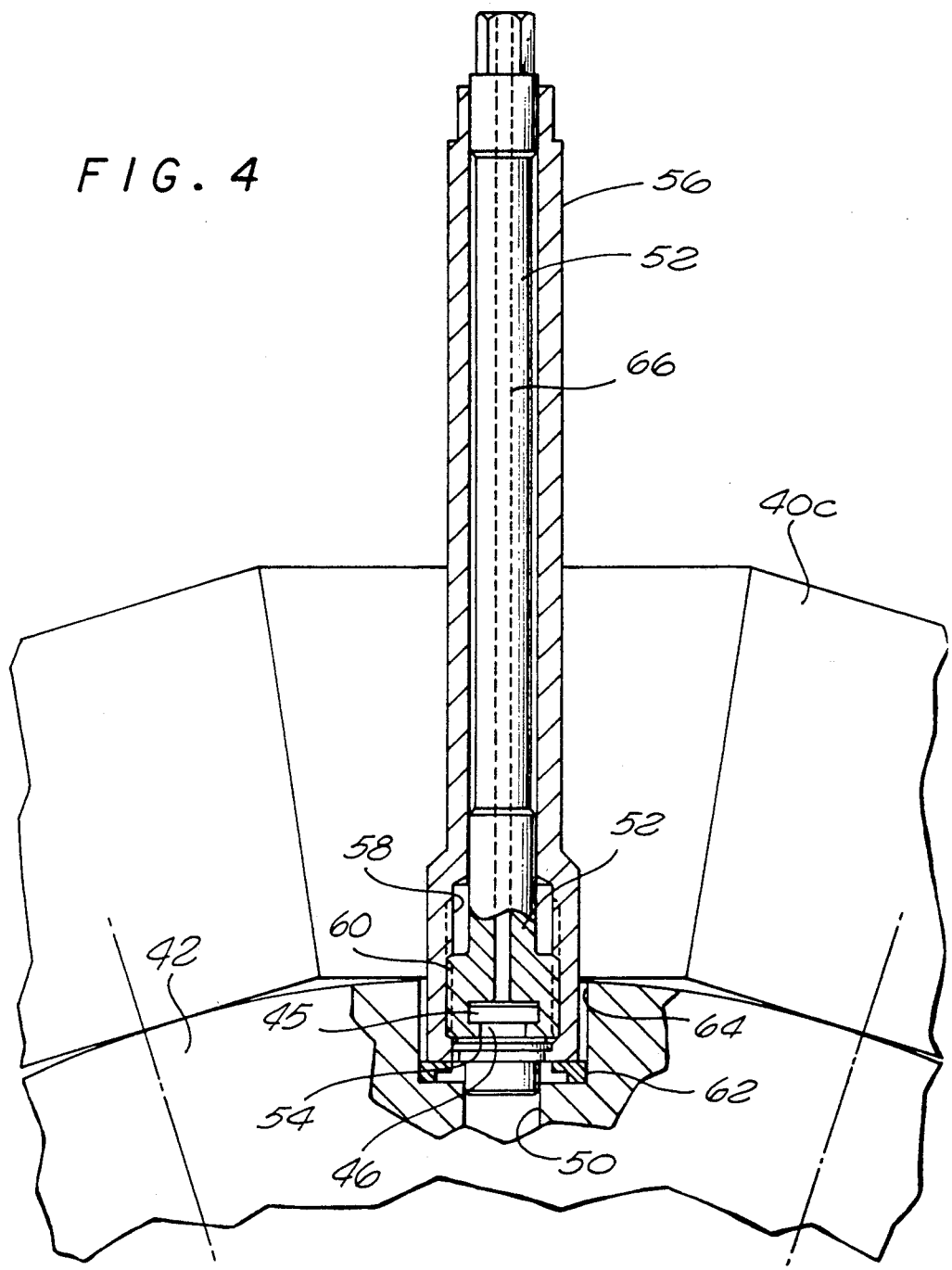
FIG. 4 is a sectional view showing mechanical source removing equipment positioned in a brain irradiating apparatus.

Referring now to FIG. 1, a typical brain irradiation apparatus 10 is shown positioned on a table 12 behind a barrier consisting of a wall 14, a six inch thick lead extension 16 above wall 14 and above the level of the apparatus 10. Above the lead extension 16, is a further barrier extension consisting of one or more blocks of lead glass 18 which are 6 inches thick. An operator 20 standing behind the barrier is enabled to view through the lead glass the apparatus 10, the radiation source removal device 22 and a remote handler 24 shown grasping the end of the source removal device 22. Alternatively, the operator may view the operation by means of a remote television set-up or with mirrors, as previously stated. Those skilled in the art will recognize that any of several operating tools may be attached at the end of the remote handlers, such as a turning or twisting head required for unthreading the radiation source or a drill driving head. The apparatus 10 includes hinged upper shield portions one of which 38 is shown open to expose the tops of the radiation source holders. To minimize radiation exposure a temporary shield 40 is placed over the radiation source holders, the temporary shield including a large number of removable sections, as discussed below. In FIG. 1, one of such removable sections has been removed and the source removal device 22 is inserted in the space available to grasp the cap of one such radiation source holder.

FIG. 2 is an end view, partly in section of brain irradiation apparatus 10 with the hinged portion of an upper shield 38 shown partly open and with temporary upper shield 40 installed over a steel or cast iron primary shield 42. Primary shield 42 contains a large number of radially arranged ports 43 in each of which is installed a radiation source and its holder. Temporary upper shield 40 includes a number of removable sections 40a, 40b and 40c, each of which is positioned over one or more radiation source holders 44, 46 and 48. As shown, removable section 40b has been displaced, exposing the cap of source holder 46. The remaining removable sections are kept in place since it is desired to minimize exposure to radiation to personnel working with the apparatus even though the sources are spent beyond the level considered useful for radiation therapy.

FIG. 3 is a fragmentary plan view of the temporary upper shield 40 showing removable sections 40a and 40c in place and with section 40b removed to expose the cap of radiation source holder 46. Other unnumbered squares indicate removable sections which are, or may be, identical with sections 40a, 40b and 40c. While only a single radiation source holder is shown in the figure, a removable section could be larger and expose a number of such source holders, preferably not exceeding four.

FIG. 4 is a sectional view showing a collet and mechanical removing equipment attached to the cap 45 of a radiation source holder 46 which is installed in a port 50 in primary shield 42. The temporary upper shield 40 is shown with sections 40a and 40c in place, but with section 40b removed. A hollow collet 52 is positioned over the cap of source holder 46 and has inwardly directed projections 54 which seat under the cap. A generally cylindrical puller 56 slides over the collet and includes inwardly directed grooves 58 which slide on splines 60 in the surface of collet 52 and force projections 54 tightly under the cap of source holder 46. A centering ring 62 forces collet 52 and puller 56 to be centered in the shallow larger diameter counterbore 64 of port 50. With the collet 52 secured to the cap 45 as described, liquid nitrogen is supplied to an interior passage 66 of the collet, coming in contact with cap 45. Cap 45 and all of the source holder 46 is of aluminum, which not only has a greater temperature coefficient than the cast iron or steel primary shield 42, but which also transfers heat more rapidly. The temperature of the source holder will drip rapidly causing it to shrink away from the wall of port 50. In most cases this will result in sufficient clearance to enable the source holder 46 to be pulled directly out of the port 50.

In some cases, the source holder 46 is threadedly engaged with threads in the upper end of port 50. Removal of source holder 46 is done in the same way as described above, except that when the cap 45 has been exposed to the liquid nitrogen for the necessary period to result in causing source holder 46 to shrink away from port 50, the puller 56 is turned to unthread the source holder 46. In either case, once the source holder is removed, it is moved by means of remote handler 24 to a suitable shielded shipping container.

Figure 5:
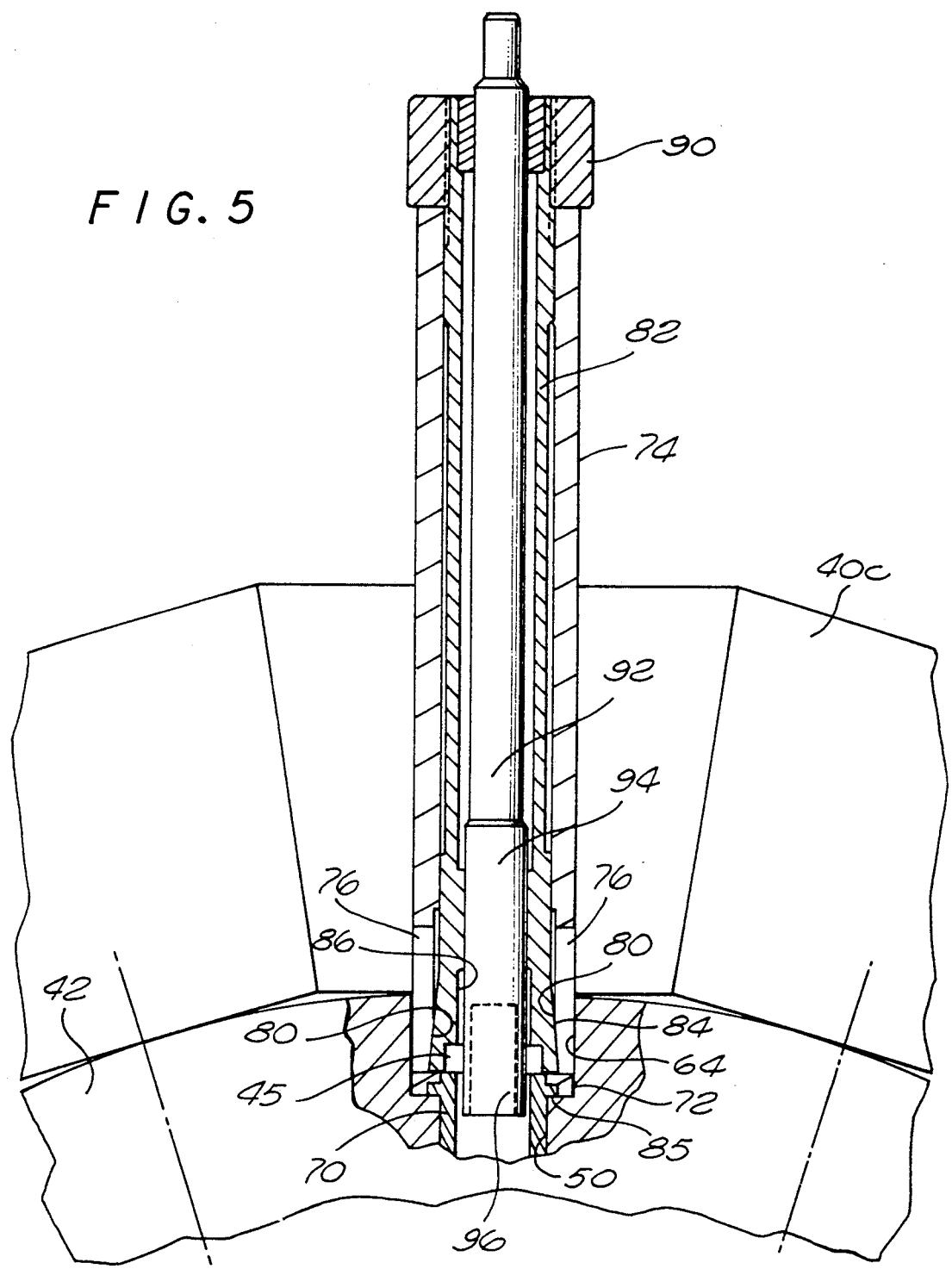
FIG. 5 is a sectional view showing another embodiment of source removing apparatus positioned in a brain irradiating apparatus

Occasionally a source holder will be so corroded or joined to the wall of port 50 that it cannot be removed by the method and means discussed above. In such situation, applicant uses the structure of FIG. 5 wherein many of the parts are the same as those of FIG. 4 and, in such cases, have been given similar numerals.

In this embodiment a steel tube liner 70 is permanently installed in the port 50 with the source holder inside. A centering ring 72 may surround the top of liner 70 and limit the travel of an expanding collet member 74 which has spreading fingers 76 having tapered inner surfaces 80 and the outer edges of which bear against the surface of counterbore 64. Except for the cap 45, the remainder of the source holder 46 is not shown. A collet draw bar member 82 is coaxially located inside of the expanding collet member 74 and at its lower end includes an outwardly tapered section 84 having an internal counterbore 86 and a second internal counterbore 88 which surrounds the cap 45. At the top of the collet draw bar member 82 is a nut 90 threadedly engaged therewith which, when turned, causes the expanding collet member 74 to move downwardly, wedging surfaces 80 against the outwardly tapered sections 84 causing them to be forced inwardly against cap 45, thus securely holding cap 45 in place. Passing through the center of collet draw bar member 82 is a drill shaft 92 which engages a hollow core drill bit 94 by means of a quick disconnect device. The external diameter of drill bit 94 is just slightly smaller than the inside diameter of steel tube liner 70 and its internal diameter 96 is just slightly larger than that of the stainless steel capsule containing the cobalt 60 source, not shown. By applying rotary power to the top end of drill shaft 92, drill bit 94 drills along the sidewalls of the aluminum source holder until it has enclosed the cobalt 60 capsule and what remains of the aluminum source holder 46, after which the entire assembly is removed from the primary shield and the hollow drill bit 94 and its contents are separated from the shaft 92 by means of the quick disconnect device, and placed in a suitable shielded container.

The above described embodiments of the present invention are merely descriptive of its principles and are not to be considered limiting. The scope of the present invention instead shall be determined from the scope of the following claims including their equivalents.

What is claimed is:

1. A method of removing radiation sources and aluminum radiation source holders mounted in ports of a primary shield of a brain irradiating apparatus, said apparatus including a top cover having removable portions, wherein said radiation source holders each include a cap and a tubular container carrying said radiation source, and securing means are provided for securing said radiation source holders to said primary shield, said method comprising:
   a) installing a portable shielded facility and a remote handler adjacent said apparatus;
   b) removing at least one portion of said top cover, exposing a plurality of said source holders;
   c) installing a new upper shield over said exposed source holders, said shield having removable sections over said source holders, and removing one of said sections, thereby exposing a source holder;
   d) providing means for viewing the source holder exposed through removal of said section;
   e) operating said handle thereby removing said securing means of said source holder exposed through removal of said section;
   f) providing means for significantly increasing the clearance between said primary shield and said source holder exposed through removal of said section, and actuating said means to increase said clearance thereby increasing the clearance between said primary shield and said source holder exposed through removal of said section;
   g) operating said handler and thereby removing said source holder exposed through removal of said section, along with said source associated with said source holder, from said primary shield; and
   h) operating said handler and thereby transferring said source holder, exposed through removal of said section with said source, to a suitable shielded container.

2. The method as claimed in claim 1 wherein step f comprises providing a hollow collet shaped to fit over and grasp said cap of said source holder, attaching said collet to said cap, introducing a low temperature liquid through said collet, thereby shrinking said source holder, and removing said low temperature liquid.

3. The method as claimed in claim 1 wherein step f comprises providing a hollow collet shaped to fit over and grasp the cap of said source holder, attaching said collet to said cap, applying a hollow mechanical puller over said collet, thereby forcing said collet to firmly grasp said cap, and introducing a low temperature liquid through said collet, thereby shrinking said source holder, and removing said low temperature liquid.

4. The method as claimed in claim 3 wherein said hollow mechanical puller is splined to the exterior surface of said collet and said handler is operated to turn said puller to unthread said source holder form said primary shield.

5. The method as claimed in claim 1 wherein step f comprises providing a drill with a hollow core drill bit whose outer diameter is smaller than the port in said primary shield receiving said source holder and whose inside diameter is larger than the diameter of said radiation source, and drilling through said source holder with said drill bit.

6. The method as claimed in claim 5 wherein step g comprises removing said drill bit, said source and said source holder and step h comprises depositing said drill bit, source and source holder in said shielded container.

7. A method of removing aluminum radiation source holders mounted in a primary shield of a brain irradiating apparatus said apparatus including a top cover having removable portions and wherein said radiation source holders each include a cap and a tubular container carrying said radiation source, and securing means are provided for securing said radiation source holders to said primary shield, said method comprising:
   a) installing a portable shielded facility and a remote handler adjacent said apparatus;
   b) removing at least one portion of said top cover, exposing a plurality of said source holders;
   c) installing a new upper shield over said exposed source holders, said shield having removable sections over said source holders, and removing one of said sections thereby exposing a source holder;
   d) providing means for viewing the source holder exposed through removal of said section;
   e) operating said handler thereby removing said securing means of said source holder exposed through removal of said section;
   f) providing a hollow collet shaped to fit over and grasp said cap of said source holder exposed through removal of said section and attaching said collet to said cap;
   g) introducing a low temperature liquid through said collet for a time sufficient to shrink said source holder exposed through removal of said section, thereby shrinking and source holder exposed through removal of said section, and then removing said liquid;
   h) operating said handler and thereby removing said source holder exposed through removal of said section from said primary shield; and
   i) operating said handler, thereby transferring said source holder exposed through removal of said section, along with said source associated with said source holder, to a suitable shielded container.

8. The method as claimed in claim 7 wherein step g comprises introducing liquid nitrogen through said collet, thereby exposing said source holder to a very low temperature for a period of approximately five to fifteen minutes after which said liquid nitrogen is removed.

9. The method as claimed in claim 7 wherein step h comprises mechanically pulling said source holder out of its seat in said primary shield.

10. The method as claimed in claim 7 wherein step h comprises applying rotary force to unthread said source holder from said primary shield.

11. For use with brain irradiating apparatus including a plurality of radiation source holders mounted in ports in a primary shield and having beam channels directed radially from said radiation sources toward a common focal point, said radiation source holders each including a cap, a radiation source carried within said aluminum source holders, means securing said aluminum source holders to said primary shield, and a top cover having removable portions to gain access to said source holders;

a method of removing said source holders from said primary shield comprising:
a) installing a portable shielded facility with viewing means and a remote handler adjacent said apparatus;
b) removing at least a portion of the top cover of said apparatus to gain access to said source holders;
c) installing a new upper shield over said source holders, said shield having removable sections over said source holders such that removal of one section will expose approximately one to four of said source holders, and removing one said section;
d) providing means for viewing the source holder exposed through removal of said section, thereby exposing a source holder;
e) using said handler to remove said securing means of said source holder exposed through removal of said section;
f) providing a hollow collet shaped to fit over and grasp said cap of said source holder exposed through removal of said section and attaching said collet to said cap;
g) introducing liquid nitrogen through said collet thereby exposing said cap to a very low temperature for a period of approximately five to fifteen minutes, thereby shrinking said source holder exposed through removal of said section, after which and then removing said liquid nitrogen;
h) operating said handler and thereby removing said source holder exposed through removal of said section from said primary shield; and
i) operating said handler and thereby transferring said source holder exposed through removal of said section, along with said source associated with said source holder, to a suitable shielded container.

* * * * *